United States Patent [19]
Céspedes et al.

[11] Patent Number: 6,165,128
[45] Date of Patent: Dec. 26, 2000

[54] METHOD AND APPARATUS FOR MAKING AN IMAGE OF A LUMEN OR OTHER BODY CAVITY AND ITS SURROUNDING TISSUE

[75] Inventors: E. I. Céspedes, Folsom, Calif.; C. L. de Korte, Driebergen-Rijsenburg; A. F. W. van der Steen, Rotterdam, both of Netherlands

[73] Assignee: EndoSonics Corporation, Rancho Cordova, Calif.

[21] Appl. No.: 09/166,016

[22] Filed: Oct. 5, 1998

[30] Foreign Application Priority Data

Oct. 6, 1997 [EP] European Pat. Off. .............. 97203072

[51] Int. Cl.[7] ...................................................... A61B 8/12
[52] U.S. Cl. ............................................................ 600/463
[58] Field of Search ................................... 600/437, 443, 600/449, 455–456; 128/916

[56] References Cited

U.S. PATENT DOCUMENTS

| | | |
|---|---|---|
| 5,125,410 | 6/1992 | Misono et al. . |
| 5,195,521 | 3/1993 | Melton, Jr. et al. .................... 600/456 |
| 5,622,174 | 4/1997 | Yamazobi ........................... 600/455 X |
| 5,800,356 | 9/1998 | Criton et al. ........................ 600/455 X |

FOREIGN PATENT DOCUMENTS

WO 94/23652  10/1994  WIPO .

OTHER PUBLICATIONS

C. L. de Korte et al., "Intravascular Elasticity Imaging Using Ultrasound: Feasibility Studies In Phantoms," Ultrasound in Medicine and Biology, vol. 23, No. 5, May 1997, USA, pp. 735–746.

K. Yamoto et al., "An Intravascular Ultrasounic Imaging Technique For Measurement Of Elastic Properties Of the Artery," Acoustical Imaging, vol. 20, Sep. 12, 1992, pp. 433–440.

L. K. Ryan et al., "A High Frequency Intravascular Ultrasound Imaging System for Investigation of Vessel Wall Properties," IEEE 1992, Ulrasonics Symposium, vol. 2, Oct. 20–23, 1992, Tucson, AZ, USA, pp. 1101–1105.

*Primary Examiner*—Francis J. Jaworski
*Attorney, Agent, or Firm*—Leydig, Voit & Mayer, Ltd

[57] ABSTRACT

Method and apparatus for making an image of a lumen and surrounding tissue in a body by inserting a transducer in the cavity and emitting ultrasound signals and collecting and processing echo signals to form an image, where the apparatus includes a signal processor arranged for performing the steps of and the method includes the steps of:

a) obtaining echo signals from tissue at a given state of mechanical stress in a chosen direction;

b) obtaining similar echo signals after a change of the mechanical stress;

c) identifying the lumen-tissue boundary;

d) comparing the echo signals to obtain a parameter indicative of tissue stiffness;

e) performing similar steps for a number of directions;

f) deriving and displaying the conventional echo image of the lumen and surrounding tissue from the echo signals of step a);

g) superimposing in said image the tissue stiffness as a coded line along the lumen-tissue boundary.

13 Claims, 6 Drawing Sheets

(6 of 6 Drawing Sheet(s) Filed in Color)

SOFT PLAQUE PHANTOM

METHOD AND APPARATUS FOR MAKING AN IMAGE OF A LUMEN OR OTHER BODY CAVITY AND ITS SURROUNDING TISSUE

The present invention relates to a method for making an image of a lumen or other body cavity and its surrounding tissue in a body wherein a transducer is inserted in the cavity and ultrasound signals are emitted by said transducer and directed towards a wall of said lumen or cavity, after which echo signals are collected and processed in a manner known per se for ultrasound techniques to form an image of the cavity and its surrounding tissue, whereas from the emitted and collected signals also information is derived concerning the stiffness of the tissue around the cavity, which information is displayed in the image that has been formed. The invention also relates to an apparatus for making an image of a lumen or other body cavity and its surrounding tissue in a body comprising a transducer arranged for insertion in the cavity and for emitting ultrasound signals to be directed towards a wall of said lumen or cavity, and for collecting echo signals, and comprising processing means arranged for processing echo signals in a manner known per se for ultrasound techniques to form an image of the cavity and its surrounding tissue, and to derive information concerning the stiffness of the tissue around the cavity from the emitted and collected signals, which information can be displayed in the image that has been formed.

A method and an apparatus of this kind are disclosed in an article in Ultrasound in Med. & Biol., Vol. 20, pp. 759–772, 1994. In said article under the title "Spectral Tissue Strain: A new technique for imaging tissue strain using intravascular ultrasound" a method and apparatus for imaging tissue strain using intravascular ultrasound is described. The strain information is displayed superimposed over the conventional echo image in the form of a colored bar graph. Both color and height of the bars indicate the average strain along one radius. Strain information is displayed on the periphery of the conventional echo image. The measurement of strain for each radius is performed for the entire depth of tissue, and therefore there is no depth resolution. The method of strain measurement is based on the change in mean scatterer spacing in tissue as a result of pulsation. Stiff tissue will deform little due to a given source of pulsation and therefore the spacing between the scatterers within that tissue will remain approximately constant. Softer tissue will deform more and the mean scatterer spacing will change correspondingly with pulsation.

The purpose of the current invention is to provide a method and apparatus of the kind as described with which it is possible to measure more accurate over a well defined layer of tissue and with a better resolution.

Elastography, is another approach related to the current invention (see for instance the articles of Cespedes et al. in Seminars in International Cardiology, 2, 55–62 and of de Korte et al. in Ultrasound in Medicine and Biology 23, 735–746 (1997). In these manuscripts, a method to produce an independent image of tissue elasticity is described. Due to the presentation of elasticity information in a separate image, a different set of advantages and limitations apply to elastography than to the method described herein. The methods and material utilized in these papers are the same ones used in the experiments presented herein. However, the algorithm and goal of the methods are substantially different.

The above goal is attained by a method in which the following steps are comprised:

a) obtaining one or more echo signals from tissue in a chosen direction, said tissue being at a given state of mechanical stress;

b) obtaining one or more echo signals from said tissue in said chosen direction, after the given state of mechanical stress has changed;

c) determining in a manner known per se of the extent of the cavity in said chosen direction in order to identify the lumen-tissue boundary;

d) comparing the echo signals from steps a) and b) starting at the lumen-tissue boundary and for a finite depth in the tissue to obtain a parameter indicative of tissue stiffness of the inner layer of tissue in said chosen direction;

e) simultaneously or successively or intermittently performing the steps a) to d) for a number of directions;

f) deriving and displaying in a manner known per se the conventional echo image of the cavity or lumen and its surrounding tissue from the echo signals obtained in step a);

g) superimposing in the image obtained in step f) the tissue stiffness as a suitable coded line along the lumen-tissue boundary or at other suitable, non-obstructive positions, and with an apparatus of which the transducer and the processing means are arranged to perform the steps of:

a) after insertion of the transducer in a lumen or cavity surrounded by its tissue obtaining one or more echo signals from tissue in a chosen direction, said tissue assumed to be at a given state of mechanical stress;

b) obtaining one or more echo signals from said tissue in said chosen direction, after the given state of mechanical stress has changed;

c) determining in a manner known per se of the extent of the cavity in said chosen direction in order to identify the lumen-tissue boundary;

d) comparing the echo signals from steps a) and b) starting at the lumen-tissue boundary and for a finite depth in the tissue to obtain a parameter indicative of tissue stiffness of the inner layer of tissue in said chosen direction;

e) simultaneously or successively or intermittently performing the steps a) to d) for a number of directions;

f) deriving and displaying in a manner known per se the conventional echo image of the cavity or lumen and its surrounding tissue from the echo signals obtained in step a);

g) superimposing in the image obtained in step f) the tissue stiffness as a suitable coded line along the lumen-tissue boundary or at other suitable, non-obstructive positions.

According to the invention a one-dimensional method is proposed to measure and display local deformation of the inner layer of the vessel wall. When possible, the thickness of this layer will encompass no less than the entire vessel wall (typically 0.5 to 1.5 mm). Additionally it is proposed to integrate the strain or elastic modulus over the entire lumen to obtain a single indicator of cross-sectional arterial stiffness. Thus, both global (cross-sectional) and local elasticity information can be obtained from IVUS (intravascular ultrasound) palpation.

Radial strain is measured from echo signals obtained at two stages of intraluminal pressure and displayed as a coded (preferably colored) profile coincident with the location of the lumen-vessel interface. The corresponding image is termed the strain palpogram. Alternatively, based on knowledge of the acting incremental pressure, the stress (pressure) to strain ratio can be calculated to obtain a quantity that resembles an elastic modulus. The corresponding image is termed the modulus palpogram.

In an embodiment of the method of the invention the given state of mechanical stress of the tissue is actively changed by expansion of a balloon in said lumen or cavity. It should be mentioned here that in U.S. Pat. No. 5,265,612 the use of a balloon is described to expand in endoluminal elasticity assessment.

In a different embodiment in which the transducer is inserted in an artery the steps a) and b) of the method of the invention are performed at different pressures in a cycle of pressure pulsation of the artery. In the above identified article by Talhami et al. also a one-dimensional approach to imaging arterial elasticity is described. Main differences between the known method and the now proposed IVUS palpation technique are the following.

IVUS palpation can measure strain by direct assessment of the deformation of tissue, whereas in Talhami's approach tissue strain is measured indirectly from the change in average spacing of the scatterers in tissue. IVUS palpation also can be used with a decorrelation approach which is indirect.

In IVUS palpation the strain or elasticity of a well defined layer of tissue is measured. The thickness of this layer is taken to include the thickness of the vessel wall or an equivalent thickness of the diseased area (plaque). This is an essential difference because the ability to measure local strain in regions of stress concentration supports one of the fundamental uses of this technique. According to the article Talhami measures the average strain for the entire thickness of tissue in the echo image. However, in the Talhami article it is mentioned that advancing the approach described to RF processing will allow to achieve some degree of depth resolution.

Probably due to the lack of depth resolution, Talhami et al. do not mention the possibility to detect (measure) areas of high stress concentration since this strain in such small areas would get averaged into the strain estimate for the entire depth.

In IVUS palpation the strain information is displayed directly at the inner surface of the artery where the measurement is performed or at other suitable, non-obstructive positions. This provides automatic and exact association of the elasticity information with respect to the echo image.

While the mechanical properties of the arteries have been extensively studied in the past, precise quantitative knowledge of this subject is still lacking. The complete description of the mechanical properties of tissue is very complicated and involves a large number of elastic constants, which are difficult or impossible to measure. In order to obtain realizable estimates of arterial elasticity, a number of simplifying assumptions are commonly accepted: the vessel wall is considered to be isotropic, homogeneous, incompressible and linearly elastic. Based on these assumptions, three prevailing measures of arterial elasticity are compliance, distensibility and pressure-strain elastic modulus. All of these measurements provide a global measure of the stiffness of the arterial cross-section since they are based on the relationship between a pressure gradient and the resulting change in luminal area. By definition these measures of arterial stiffness do not take into consideration the thickness of the arterial wall or plaque. However, their prevalence implies that reasonably useful information on the elasticity of the artery can be obtained even when the thickness is ignored.

In the following measures of the elastic properties of the arterial wall incorporating a finite thickness of tissue are described. The local incremental pressure-strain elastic modulus is defined as $$E = \frac{\Delta P}{\varepsilon}, \quad (1)$$

where $\Delta P$ is the pressure change and $\varepsilon$ is the resulting strain. Since in general the stress strain ratio is nonlinear, this incremental p-s modulus is a function of the mean value of the stress.

The local radial strain in the arterial wall is given by $$\varepsilon = \frac{\Delta R_2 - \Delta R_1}{R_2 - R_1}, \quad (2)$$

where $\Delta R_1$ is the displacement of the inner layer of wall tissue, $\Delta R_2$ is the displacement at a deeper location in arterial wall and $R_2 - R_1$ is the distance between range gates. The above elastic modulus refers to the stiffness of the artery wall per se, while other mechanical measures such as compliance and distensibility refer to the stiffness of the artery as a hollow structure.

In practice, most arteries requiring ultrasonic evaluation are abnormal to some extent and contain focal or diffuse atherosclerotic disease or arteriosclerosis. Except for few cases, the thin-walled tube approximation is not valid and local stress and strain values can be disproportionally large. Nevertheless, useful conceptual information can be obtained from idealized models of blood vessels. In an isotropic tube, the radial component of strain is given by $$\varepsilon_r = \left(\frac{1}{E}\sigma_r - v\sigma_\theta - v\sigma_z\right), \quad (3)$$

where $\sigma_r$, $\sigma_\theta$, and $\sigma_z$ are the stress components in the radial circumferential and longitudinal directions, respectively. Notice that radial strain is compressive and circumferential and longitudinal stresses are tensile. This equation indicates that when any stress component increases a corresponding increase in radial strain can be expected. Thus, the strain palpogram has the potential to be a good indicator of increased focal, omnidirectional stress.

Global measures of elasticity in diseased arteries will deviate from normal values as a result of focal disease. Consequently, in order to obtain a unified quantitative measure of the overall stiffness of the cross-section we define the integrated pressure-strain modulus as $$E_{avg} = \frac{\Delta P}{\varepsilon_{avg}}, \quad (4)$$

where $$\varepsilon_{avg} = \frac{1}{2\pi}\int_\theta \varepsilon(\theta)d\theta, \quad (5)$$

In general, the integrated pressure-strain modulus does not directly correspond to any conventional measure of elasticity, but in the case of a uniform, isotropic, elastic artery it would correspond to the Young's modulus. Nevertheless, the mechanical properties of a plaque can be expected to inflict a noticeable change in the cross-sectional measure of arterial stiffness. Because $E_{avg}$ is an overall measure of the local elastic modulus of the artery wall per se, it may be a more reliable indicator of the mechanical properties of the constituent tissues than compliance or distensibility which totally ignore the contribution of wall thickness.

The invention will be described in details with reference to the accompanying drawings, in which the file of this patent contains at least one drawing executed in color.

Figure 4:
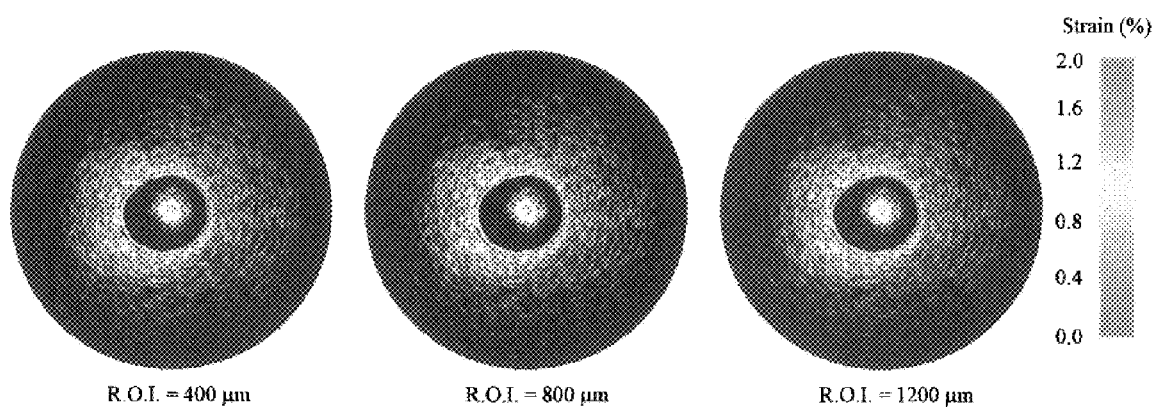
Figure 5:
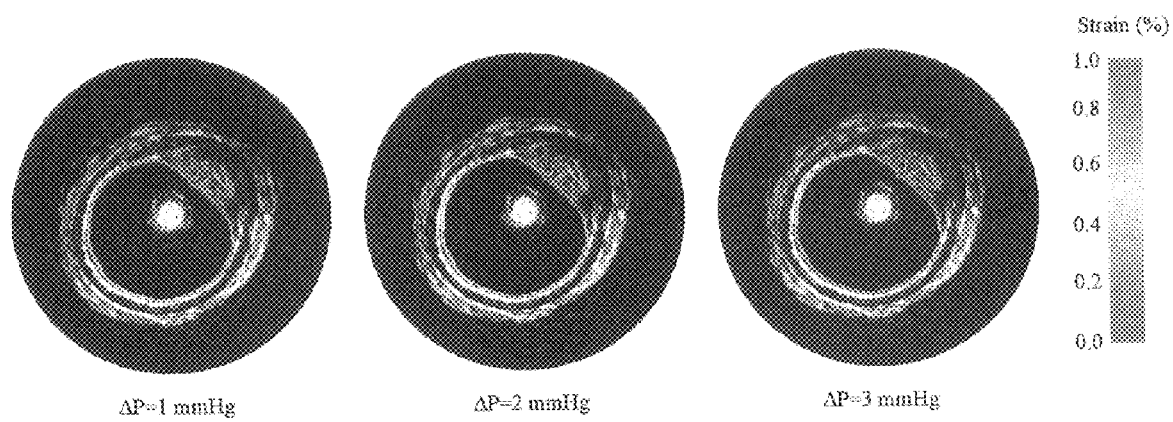
Figure 6:
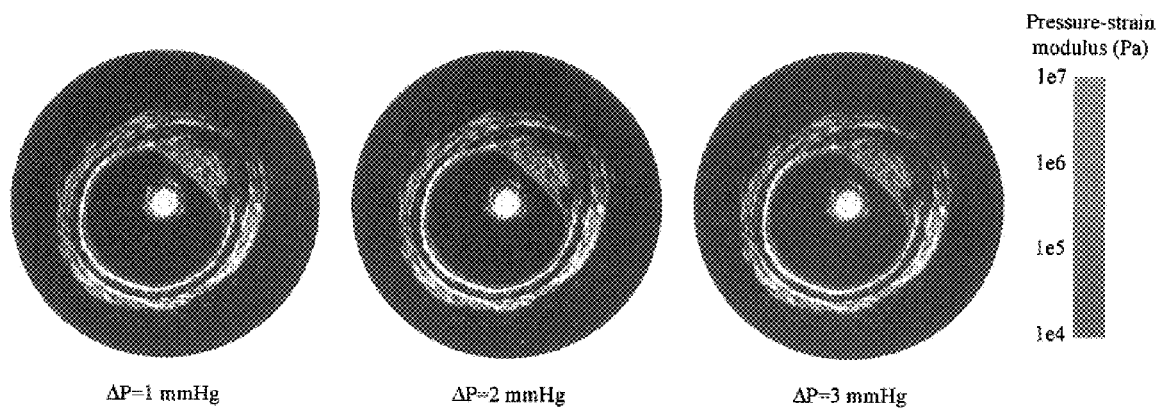

FIG. 4 shows strain palpograms of vessel phantom containing a hard plaque obtained using three different regions of interest (layer thickness: 0.4, 0.8 and 1.2 mm); FIG. 5 shows IVUS images and strain palpograms of an iliac artery specimen with a stiff plaque at three intraluminal pressure differentials (1, 2 and 3 mm Hg), and FIG. 6 shows IVUS images and pressure-strain modulus palpograms of an iliac artery specimen with a stiff plaque at three levels of intraluminal pressure differentials (1, 2 and 3 mm Hg)

In order to evaluate the feasibility of intravascular ultrasonic palpation, an experimental framework was utilized based on a clinical IVUS system. The set-up was used to image gel-based vessel mimicking phantoms and an artery specimen. These were scanned in the water tank at several states of static intraluminal pressure. These intraluminal pressures can be interpreted as the pressure state at specific time intervals during arterial pulsation or as the pressure state at different pressurizations of a balloon.

Vessel phantoms were constructed from solutions of agar and gelatin in water with carborundum (SiC) particles used for scattering. Combining plastic tubes of different diameters, gels were molded into vessel-like structures. The phantom materials and construction method have been described elsewhere. Additionally, a 45 mm long human iliac artery specimen was dissected and frozen. The specimen contained a plaque that was palpable externally. After thawing, the iliac specimen was scanned at room temperature. Following standard procedure, histology slides were obtained by staining and demonstrate a fibrous atheroma.

The experimental set-up consisted of a water tank equipped with sheaths (8F) at two opposite sides to which the phantom or specimens were securely attached. A 4.3F, 30 MHz, intravascular catheter (EndoSonics, The Netherlands) was inserted through one sheath and into the lumen of the phantom. This sheath was also connected to a variable water-column system for intraluminal pressurization of the phantom. Static pressurization levels were used for compression: a strain on the order of 1% was achieved by a change in pressure of 4 mm Hg. The artery specimen was pressurized from 95 to 98 mm Hg in 1 mm Hg steps.

The IVUS catheter was connected to a modified Intrasound IVUS scanner (EndoSonics, The Netherlands) with a stepper-motor unit that was set to scan the vessel at 400 steps/revolution. The radiofrequency (rf) echo signals were digitized at 100 MHz, 8 bits using a digital oscilloscope (LeCroy 9400, LeCroy, Spring Valley, N.Y.) and stored in a personal computer for off-line processing and display.

Figure 1:
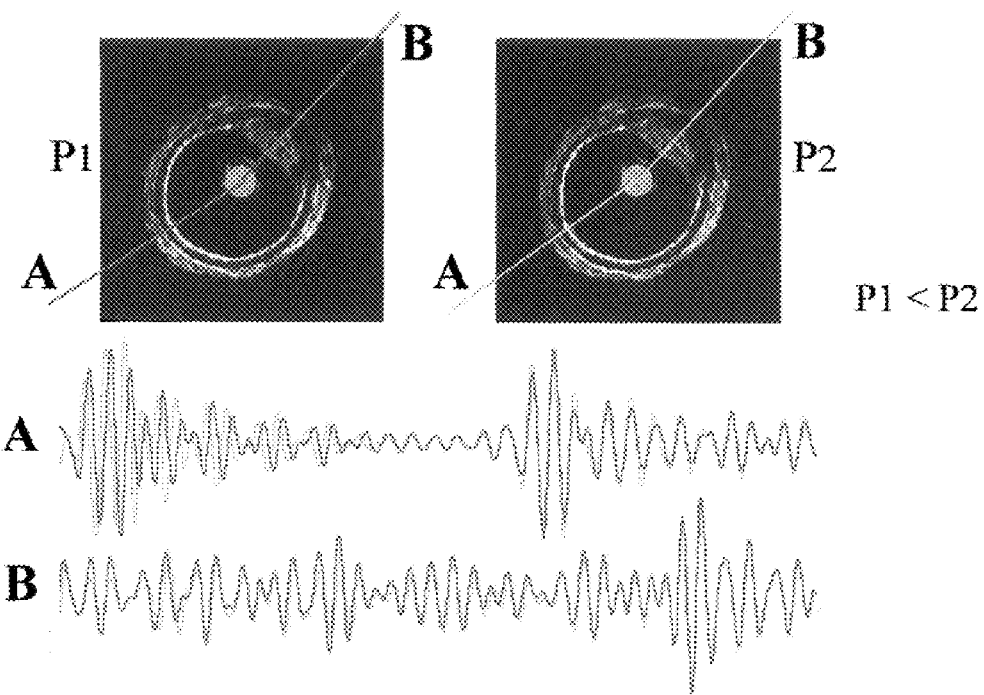
FIG. 1 shows IVUS images of an iliac artery specimen obtained at two levels of intraluminal pressure (pressure change of 2 mm Hg) with rf echo signals.

Generally, temporal shifts of the echo signals are related to the corresponding displacements of the tissue originating the echoes. Under the effect of an intraluminal pressure differential, stiff tissues will deform less than softer tissues. This is illustrated in FIG. 1, where two IVUS images of the iliac artery specimen obtained at different intraluminal pressures are shown. The echo signals from two selected angles corresponding to normal wall and stiff plaque are also shown. As a result of the pressure increment, the distance between echoes from within the normal arterial wall appears to be compressed, while the echoes from stiffer plaque show little change in relative position. Note that this overt difference in the position of the echoes is practically undetectable on the IVUS images.

Strain, pressure-strain modulus and the average pressure strain modulus are calculated using Eqs. (1) to (4). Two rf range gates along a line of sight extending the vessel wall or sufficiently long to include the vessel wall and an equivalent part of the plaque are utilized to estimate the time shift. These range gates can be chosen to be overlapping or not, and from contiguous or disjoint regions of the artery. The difference between the time shift divided by the distance between the range gates is the wall strain. The beginning of tissue is easily detected in vitro since blood is replaced by echo free saline. Then, a simple amplitude thresholding algorithm is used to identify the lumen. Starting at the lumen, the default analysis thickness was 1 mm. Additionally, to investigate the dependence of the palpogram on the analysis thickness, the results from one phantom were obtained using tissue layers of 0.4 mm, 0.8 mm and 1.2 mm.

On the echo images of FIG. 1 two angles which correspond to relatively normal vessel wall (labeled A) and fibrous plaque (labeled B) are identified with dashed lines. The rf echo signal pairs at those angular position are also shown. It is clear that while the echoes from direction A appear compressed, those from direction B have suffered little change. These changes are not visible from the echo images. FIG. 1 also shows that discrimination of softer and stiffer tissue is possible with rf processing. The discussion will be concentrated on rf processing. However, the robustness and decreased precision of time delay estimation with envelope processing may be well suited for IVUS palpation.

Figure 2:
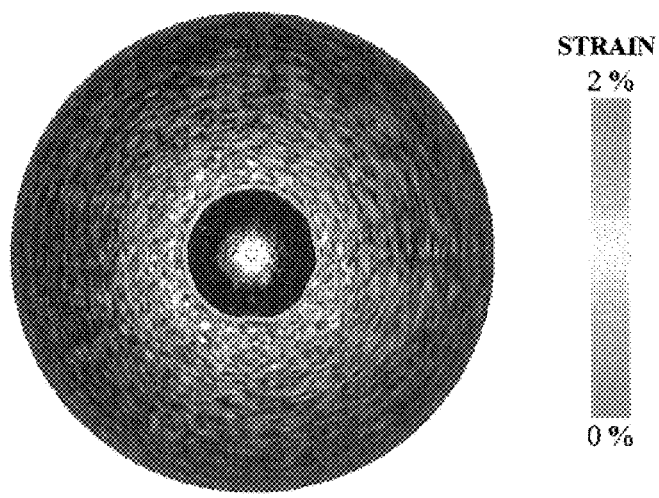
FIG. 2 shows IVUS image and strain palpogram of a vessel phantom of uniform elasticity and echogenicity.

In FIG. 2 an endoluminal image with strain palpogram of a uniform vessel phantom void of lesions is shown. The palpogram shows a constant strain in the phantom wall in correspondence to the uniform stiffness of the phantom.

Figure 3:
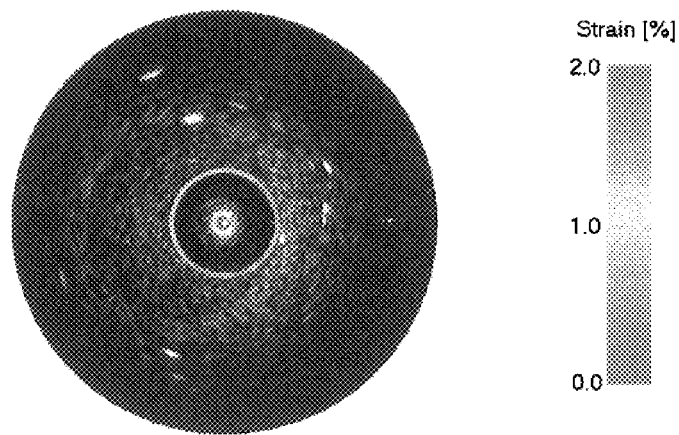
FIG. 3 shows IVUS image and strain palpogram of a vessel phantom containing a soft plaque with echogenicity contrast.

In FIG. 3 an IVUS image with strain palpogram of a vessel phantom with a soft plaque is shown. The plaque is isoechoic and therefore cannot be seen in the echo image. However, the palpogram demonstrates increased strain, easily identifying the region of decreased stiffness.

FIG. 4 shows the palpograms of a vessel phantom with a hard plaque calculated with depths (layer thickness) of 0.4 mm, 0.8 mm and 1.2 mm. A small, albeit noticeable change in the location of the plaque as a function of the analysis thickness can be noticed. However, all palpograms correctly identify the plaque as stiffer than the rest of the phantom increased strain, thus satisfying the objective of the imaging approach.

FIG. 5 shows the IVUS strain palpograms obtained at increasing pressures. Notice the increase in strain, particularly in the normal wall. Little change is visible in the stiff plaque. Regions of increased strain are shown around the edges of the plaque. Strain increases with increased luminal pressure, particularly in the plaque-free region of the wall.

In FIG. 6, the corresponding pressure-strain modulus palpograms are shown. Note that after conversion to the modulus the presentation of the palpogram is very similar at all three pressurizations. The respective average pressure strain modulus were 78, 83 and 97 kPa. Note the clear identification of the fibrous plaque as stiff. Although the plaque is also easily identified in the echo image, biomechanical information is added without disturbing the original presentation of the IVUS image.

The ultimate goal of elasticity imaging is to assess the local deformation and/or modulus of elasticity of tissue. In general, the linear elasticity properties of tissue is fully characterized by several elastic constants which can only be calculated with knowledge of the three-dimensional state of stress and strain; furthermore, tissue is viscoelastic and nonlinear. In practice, the internal stress in tissue cannot be measured and ultrasonic measurement of strain is limited to precise estimation of the strain component along the direction of the ultrasound beam. Thus, any practicable approach must support a number of assumptions with a resulting accuracy consistent with the expected deviations.

In the past, strain imaging has been performed as a practical substitute for elastic modulus imaging because the local stress components were unknown. However, modulus imaging was considered the optimal technique because it depicts a basis property of the tissue. Here, an important clinical application is identified where the strain, rather than the modulus, is important. Therefore, in the context of imaging of vulnerable plaques, the strain palpogram is advantageous over the elastic modulus palpogram. For characterization of plaque composition, the modulus palpogram may be more adequate.

Endoluminal ultrasound is routinely used in several non-vascular applications, e.g., transrectal, endovaginal, endoesophageal, transurethral. With advances in the miniaturization of endoluminal devices, applications of ultrasound diagnosis from within one body are certainly on the rise. Analogously to the situation in intravascular imaging, additional information on the stiffness of pathologies is useful in urologic and gastrointestinal applications. Although the technique of ultrasonic palpation has been described in the context of intravascular application, the same principles can be utilized in other areas. In fact, the phantoms presented which are intended to emulate blood vessels could also be construed to be scaled versions of other cavities such as the ureter or the esophagus. Lacking the pressure source provided by the pulsation of blood and the acoustic contact provided by blood, a fluid-filled balloon should be utilized to apply the probing deformation of the tissues and acoustic coupling. Thus, ultrasonic palpation of the ureter or the esophagus, for example, would be a feasible and interesting area of investigation. In fact, a similar situation arises in the assessment of esophageal tumors where ultrasound endoscopy is able to identify the extent but not the characteristic of the disease.

Strain palpograms of an iliac artery specimen demonstrate the ability of IVUS palpation to measure local deformation of the vessel wall and atheroma. Despite the low magnitude of the effect, regions of stress concentration can be identified at the shoulders of the plaque. In plaques with lipid contents, identification of areas of stress concentration is one main indicator of plaque vulnerability and no method to obtain this information in vivo is presently available.

The simplicity and robustness associated with the ultrasonic palpation concept may allow advancement to a real-time implementation with which the true potential of the method can be adequately explored in the clinical environment.

We claim:

1. A method for making an image of a lumen or other body cavity and its surrounding tissue in a body wherein a transducer is inserted in the lumen or cavity and ultrasound signals are emitted by said transducer and directed towards a wall of said lumen or cavity, after which echo signals are collected and processed to form an image of the lumen or cavity and its surrounding tissue, whereas from the emitted and collected signals also information is derived concerning the stiffness of the tissue around the lumen or cavity, which information is displayed in the image that has been formed, comprising the steps of:

a) obtaining one or more echo signals from tissue in a chosen direction, said tissue being at a given state of mechanical stress;

b) obtaining one or more signals from said tissue in said chosen direction, after the given state of mechanical stress has changed;

c) determining the extent of the lumen or cavity in said chosen direction in order to identify the lumen-tissue or cavity-tissue boundary;

d) comparing the echo signals from steps a) and b) starting at the lumen-tissue or cavity-tissue boundary and for a finite depth in the tissue to obtain a parameter indicative of tissue stiffness of the inner layer of tissue in said chosen direction;

e) performing the steps a) to d) for a number of directions;

f) deriving and displaying the echo image of the cavity or lumen and its surrounding tissue from the echo signals obtained in step a); and g) presenting in the image obtained in step f) the tissue stiffness as a one-dimensional coded line along the lumen-tissue or cavity-tissue boundary.

2. The method of claim 1, wherein the coded line has a color code applied to indicate tissue stiffness.

3. The method of claim 1, wherein the state of mechanical stress in steps a) and b) is accomplished by expansion of a balloon in said lumen or cavity.

4. The method of claim 1 wherein the lumen or cavity comprises an artery and the transducer is inserted in the artery, and said steps a) and b) are performed at different pressures within a cycle of pressure pulsation of the artery.

5. The method of claim 1, wherein in step d) use is made of relative displacement of said echo signals from steps a) and b)in order to determine the tissue stiffness.

6. The method of claim 5, wherein the determination of tissue stiffness is made by using the displacement of a peak in an amplitude image of said echo signals.

7. The method of claim 1, wherein the tissue stiffness is determined by using decorrelation measurements.

8. Apparatus for making an image of a lumen or other body cavity and its surrounding tissue in a body comprising a transducer arranged for insertion in the lumen or cavity and for emitting ultrasound signals to be directed towards a wall of said lumen or cavity, and for collecting echo signals, and comprising processing means arranged for processing echo signals to form an image of the lumen or cavity and its surrounding tissue, and to derive information concerning the stiffness of the tissue around the lumen or cavity from the emitted and collected signals, which information can be displayed in the image that has been formed, wherein the transducer and the processing means are arranged to perform the steps comprising of:

a) after insertion of the transducer in a lumen or cavity surrounded by its tissue obtaining one or more echo signals from tissue in a chosen direction, said tissue assumed to be at a given state of mechanical stress;

b) obtaining one or more echo signals from said tissue in said chosen direction, after the given state of mechanical stress has changed;

c) determining in a manner known per se of the extent of the cavity in said chosen direction in order to identify the lumen-tissue boundary;

d) comparing the echo signals from steps a) and b) starting at the lumen-tissue boundary and for a finite depth in the tissue to obtain a parameter indicative of tissue stiffness of the inner layer of tissue in said chosen direction;

e) performing the steps a) to d) for a number of directions;

f) deriving and displaying the conventional echo image of the cavity or lumen and its surrounding tissue from the echo signals obtained in step a);

g) presenting in the image obtained in step f) the tissue stiffness as a one-dimensional coded line along the lumen-tissue boundary.

9. A method for making an image of an arterial lumen and its surrounding tissue wherein a transducer is inserted in the arterial lumen and ultrasound signals are emitted by said transducer and directed towards a wall of said arterial lumen, comprising the steps of:

a) obtaining one or more echo signals from tissue in a chosen direction, said tissue being at a given state of mechanical stress during a particular cardiac cycle;

b) obtaining one or more signals from said tissue in said chosen direction, after the given state of mechanical stress has changed during the same cardiac cycle as in step a);

c) determining the extent of the arterial lumen in said chosen direction in order to identify the lumen-tissue boundary;

d) comparing the echo signals from steps a) and b) starting at the lumen-tissue boundary and for a finite depth in the tissue to obtain echo time shift information used in calculating a parameter indicative of tissue stiffness of the tissue in said chosen direction;

e) performing the steps a) to d) for a number of directions;

f) deriving and displaying the echo image of the arterial lumen and its surrounding tissue from the echo signals obtained in step a); and g) presenting in the image obtained in step f) the tissue stiffness.

10. A method as defined in claim 9, wherein the echo time shift information in step d) is determined by using at least two range gates.

11. A method as defined in claim 10, wherein the coded line along the lumen-tissue boundary is color coded to indicate different tissue stiffness areas.

12. A method as defined in claim 10, wherein the the tissue stiffness as a coded line along the lumen-tissue boundary.

13. A method as defined in claim 12, wherein the echo time shift information obtained in step d) is divided by the distance between the at least two range gates in order to determine the parameter indicative of tissue stiffness.

* * * * *